US 6,402,779 B1

(12) United States Patent
Colone et al.

(10) Patent No.: US 6,402,779 B1
(45) Date of Patent: Jun. 11, 2002

(54) BALLOON-ASSISTED INTRALUMINAL STENT GRAFT

(75) Inventors: William M. Colone; Kevin G. Farl, both of Phoenix; Barbara L. Teeter, Tempe; William L. Creer, Phoenix; Joseph B. Sinnott, Tempe, all of AZ (US)

(73) Assignee: Endomed, Inc., Phoenix, AZ (US)

( * ) Notice: Subject to any disclaimer, the term of this patent is extended or adjusted under 35 U.S.C. 154(b) by 0 days.

(21) Appl. No.: 09/361,192

(22) Filed: Jul. 26, 1999

(51) Int. Cl.[7] ................................................. A61F 2/06
(52) U.S. Cl. ...................................... 623/1.49; 623/1.1
(58) Field of Search ...................... 623/1.1, 901, 1.49, 623/1.32

(56) References Cited

U.S. PATENT DOCUMENTS

| 3,657,744 A | 4/1972 | Ersek |
| 3,953,566 A | 4/1976 | Gore |
| 4,140,126 A | 2/1979 | Choudhury |
| 4,187,390 A | 2/1980 | Gore |
| 4,482,516 A | 11/1984 | Bowman et al. |
| 4,544,711 A | 10/1985 | Mancinelli |
| 4,580,568 A | 4/1986 | Gianturco |
| 4,617,932 A | 10/1986 | Kornberg |
| 4,655,771 A | 4/1987 | Wallsten |
| 4,800,882 A | 1/1989 | Gianturco |
| 4,907,336 A | 3/1990 | Gianturco |
| 4,955,899 A | 9/1990 | Della Corna et al. |
| 5,019,085 A | 5/1991 | Hillstead |
| 5,122,154 A | 6/1992 | Rhodes |
| 5,123,917 A | 6/1992 | Lee |
| 5,152,782 A | 10/1992 | Kowligi et al. |
| 5,302,317 A | 4/1994 | Boller et al. |
| 5,316,023 A | 5/1994 | Palmaz et al. |
| 5,415,664 A | 5/1995 | Pinchuk |
| 5,484,444 A | 1/1996 | Braunschweiler et al. |
| 5,489,295 A | 2/1996 | Piplani et al. |
| 5,507,767 A | 4/1996 | Maeda et al. |
| 5,507,771 A | 4/1996 | Gianturco |
| 5,575,816 A | 11/1996 | Rudnick et al. |
| 5,609,627 A | 3/1997 | Goicoechea et al. |

(List continued on next page.)

FOREIGN PATENT DOCUMENTS

| EP | 0893108 A2 | 1/1999 | |
| WO | WO92/19310 | 11/1992 | |
| WO | WO 95/05555 | 2/1995 | |
| WO | WO-96/00103 | * 1/1996 | .......... A61M/29/00 |
| WO | WO 98/00090 | 1/1998 | |
| WO | WO 98/27894 | 2/1998 | |
| WO | WO 98/26731 | 6/1998 | |
| WO | WO98/31305 | 7/1998 | |
| WO | WO 98/31306 | 7/1998 | |
| WO | WO98/36708 | 8/1998 | |
| WO | WO 98/38947 | 9/1998 | |
| WO | WO 99/32051 | 7/1999 | |

OTHER PUBLICATIONS

Alexis Carrel, "Results of the permanent intubation of the thoracic aorta", Surgery, Gynecology and Obstetrics, vol. XV, No. 3, Sep. 1912, pp. 245–248.

*Primary Examiner*—Corrine McDermott
*Assistant Examiner*—Thomas Barrett
(74) *Attorney, Agent, or Firm*—David E. Rogers; Stuart A. Whittington; Squire, Sanders & Dempsey, L.L.P.

(57) ABSTRACT

An intraluminal device such as a stent graft is formed of a conformable ePTFE tube and preferably a compressed self-expanding stent affixed to the tube. The conformable tube is made by a special process which insures that the tube is radially deformable up to a predetermined diameter without exceeding the plastic deformation limit of the tube. The stent has a relaxed diameter larger than the diameter of the expanded tube after insertion so that the tube is biased to a cylindrical shape. The process for making the tube involves progressively dilating a small diameter extruded tube until a desired diameter is achieved. The tube is then contracted on a small diameter mandrel by heating.

28 Claims, 4 Drawing Sheets

U.S. PATENT DOCUMENTS

| | | |
|---|---|---|
| 5,632,763 A | 5/1997 | Glastra |
| 5,639,278 A | 6/1997 | Dereume et al. |
| 5,662,713 A | 9/1997 | Andersen et al. |
| 5,695,517 A | 12/1997 | Marin et al. |
| 5,700,269 A | 12/1997 | Pinchuk et al. |
| 5,700,285 A | 12/1997 | Myers et al. |
| 5,718,724 A | 2/1998 | Goicoechea et al. |
| 5,749,880 A | 5/1998 | Banas et al. |
| 5,755,734 A | 5/1998 | Richter et al. |
| 5,776,142 A | 7/1998 | Gunderson |
| 5,800,512 A | 9/1998 | Lentz et al. |
| 5,824,037 A | 10/1998 | Fogarty et al. |
| 5,827,320 A | 10/1998 | Richter et al. |
| 5,833,694 A | 11/1998 | Poncet |
| 5,873,906 A | 2/1999 | Lau et al. |
| 5,906,640 A | 5/1999 | Penn et al. |
| 5,906,641 A | 5/1999 | Thompson et al. |
| 5,916,263 A | 6/1999 | Goicoechea et al. |
| 6,139,573 A * | 10/2000 | Sogard et al. ............. 623/1.13 |

* cited by examiner

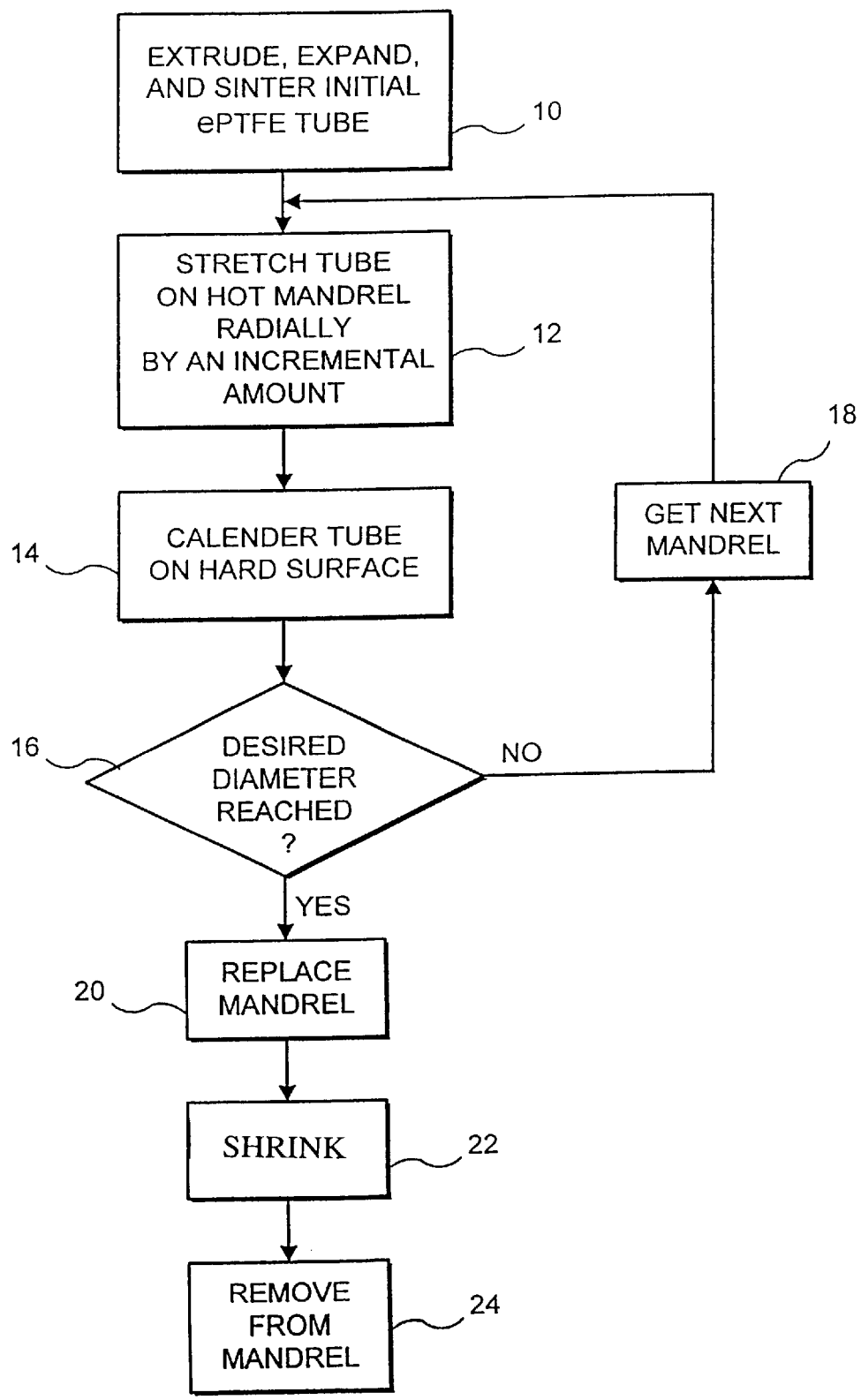
F I G. 1

BALLOON-ASSISTED INTRALUMINAL STENT GRAFT

BACKGROUND OF THE INVENTION

A. Field of Invention

This invention relates to the field of intraluminal devices and particularly to intraluminal grafts useful as an inner lining for blood vessels or other body conduits. More particularly, the present invention provides tubular structures which can be expanded in a transversal direction to conform to the diameter of a particular vessel in a patient's anatomy.

B. Description of the Prior Art

Conventional vascular grafts have been used routinely for the repair of the human vasculature. These devices are typically flexible tubes of woven or knitted polyethylene terephthalate (PET or Dacron ®), porous polytetrafluoroethylene (PTFE) or porous polyurethane (PU). Grafts of biological origin have also been used, typically comprising preserved human umbilical or bovine arteries. These conventional vascular grafts usually require invasive surgical procedures for insertion to expose at least the two ends of the segment of vessel to be repaired. Frequently, it is necessary to expose the entire length of the vessel segment. These types of procedures can cause major trauma to the patient with corresponding lengthy recovery periods, and may result in occasional mortality. In addition, grafts of various sizes are required to conform to the specific vasculature of a patient.

Other methods have evolved which use intraluminal vascular grafts, adjustable stents providing structural support, or a combination of both. These devices are preferably remotely introduced into a body cavity using a catheter type of delivery system. Alternatively, these devices may be directly implanted by invasive surgery. The intent of these methods is to maintain patency after an occluded vessel has been reopened using balloon angioplasty, laser angioplasty, atherectomy, roto-ablation, invasive surgery, or a combination of these treatments.

Intraluminal vascular grafts can also be used to repair and provide structural support to aneurysmal vessels, particularly aortic arteries, by inserting an intraluminal vascular graft within the aneurysmal vessel so that it can withstand the blood pressure forces responsible for creating the aneurysm. In this environment, intraluminal vascular grafts provide new blood contacting surfaces within the lumen of a diseased living vessel. Moreover, intraluminal grafts are not limited to blood vessels, but have other applications, such as the repair and reconstruction of urinary tracts, biliary ducts, respiratory tracts and the like.

In the prior art, an intraluminal graft is collapsed and inserted into a body conduit at a smaller diameter at a location remote from the intended repair site. A catheter type of delivery system is then used to move the intraluminal graft into the repair site and then expand its diameter to conform to the inner surface of the living vessel. Various attachments, including adjustable stents or barbs, may also be used to secure the intraluminal graft to the subject vessel at the desired location without the necessity of invasive surgery.

Various attempts have been made to provide intraluminal vascular grafts with or without stents. For example, an intraluminal vascular graft was suggested as early as 1912 in an article by Alexis Carrel ("Results of the permanent intubation of the thoracic aorta", Surg., Gyn. and Ob. 1912;15:245–248).

Ersek (U.S. Pat. No. 3,657,744) describes a method of using one or more stents to secure a flexible fabric vascular graft intraluminally, the graft and stent having been introduced distally and delivered to the desired position with a separate delivery system. According to this patent, the graft is introduced to the patient at its final diameter, since the device is placed following surgical exposure and resection of the injury site. The stents are mechanically deployed by twisting an external apparatus.

Choudhury (U.S. Pat. No. 4,140,126) describes a similar method of repairing aortic aneurysms whereby a PET vascular graft is fitted at its ends with metal anchoring pins and pleated longitudinally to collapse the graft to a size small enough to allow for distal introduction. The barbed anchoring pins are deployed by advancing a wire to mechanically increase the diameter of the rings.

Rhodes (U.S. Pat. No. 5,122,154), describes endovascular bypass grafts for intraiuminal use which comprises a sleeve made of standard graft material and unidirectionally hinged stents. The graft is longitudinally pleated for introduction, and the stents are expanded in location by external means.

Lee (U.S. Pat. No. 5,123,917) describes an intraluminal vascular graft made of flexible, radially expandable material and balloon-expandable stents. The material and stents are both radially expanded in situ using, e.g., a balloon.

Gianturco (U.S. Pat. No. 5,507,771), describes a self-expanding stent assembly with an elastic covering for the prevention of restenosis. The entire device fully self-expands upon deployment.

Meyers (U.S. Pat. No. 5,700,285) describes a seamed, thin walled intraluminal PTFE graft with balloon expandable stents. A balloon is employed to expand the graft and stents in location.

Banas (U.S. Pat. No. 5,749,880) similarly describes a reinforced vascular graft with radially expandable PTFE coupled with balloon expandable stents. The graft and stents are stretched beyond their plastic limits by a balloon to deploy the device.

Fogarty (U.S. Pat. No. 5,824,037) describes modular tubular prostheses made of radially expandable cloth material and self-expanding stents. The graft material is expanded by balloon, and the stents provide radial support for the reoriented cloth fibers.

Martin (European Patent Application EP 0893108 A2,) describes a stent-graft with a ribbon affixing a portion of a stent to a PTFE graft.

All of these devices have a number of drawbacks that make them undesirable for clinical use. First, devices made of non-expandable materials and having predetermined deployed diameters cannot accommodate variations in patient physiology, and changes in diameter between the distal and proximal implantation site.

Second, devices with plastically deformable stents cannot withstand external compression without deformation of the stents, limiting the use of the devices in patient's extremities.

Third, fully self-expanding devices must be deployed through a sheath, which typically compels the user to deploy the devices linearly, i.e. from the proximal to the distal end.

SUMMARY OF THE INVENTION

Therefore, it would be advantageous to provide an intraluminal device having a diameter which can be adjusted in vivo. It is further desirable to provide a device that is self-expandable so that it can recover from external compression. It is still further desirable to provide a device which can be deployed in a non-linear fashion, i.e., first attaching the proximal end, then attaching the distal end, and, finally adjusting the diameter of the device between the two ends.

It is an objective of the present invention to provide an intraluminal device which has initially a small diameter so that it can be introduced easily into the vessel of a patient from a remote location and which can be easily expanded in place to any desired diameter thereby conforming to the diameter of the vessel being repaired or reinforced.

A further objective is to provide an intraluminal device such as a stent graft including a conformable ePTFE tube and a self-expandable support stent.

A further objective is to provide a novel process for making a conformable ePTFE tube usable as an intraluminal device which can be radially deformed easily up to a preset diameter without exceeding its plastic deformation limit.

Other objectives and advantages of the invention shall become apparent from the following description of the invention.

An intraluminal device constructed in accordance with this invention includes at least one self-expanding stent affixed to a tube formed of a porous, conformable ePTFE. The term 'conformable ePTFE tube' shall be used herein to define a tube made from ePTFE using a particular process described below.

Porous ePTFE has a microstructure of nodes interconnected by fibrils, as taught in U. S. Pat. Nos. 3,953,566; 4,187,390 and 4,482,516. Typically, tubes of ePTFE have been made using a combined extrusion and longitudinal stretching process. A problem with these types of tubes is that because of the limitations of the machinery and processes used to produce them, their wall thickness becomes large once the tube diameters exceed 8 mm and hence cannot be used for many prostheses requiring grafts of up to 25 mm in diameter. Moreover, standard ePTFE tubes cannot be expanded radially because they have a tendency to lose strength and split when they are dilated.

A method of producing dilated ePTFE tubes with much larger diameters (up to 25 mm and more) with extremely thin walls (down to 0.008 inches and less) by progressive dilation of an initial ePTFE tube by an incremental amount followed by, calendering at a preselected temperature is taught by co-pending commonly assigned U. S. Pat. No. Application 09/244,343 by Colone et al. entitled "METHOD OF MAKING LARGE DIAMETER VASCULAR PROSTHESES AND A VASCULAR PROSTHESIS MADE BY SAID METHOD" filed Feb. 4, 1999, now U.S. Pat. No. 6,187,054, issued Feb. 13, 2001 and incorporated herein by reference.

In the present invention, an ePTFE tube which has been dilated by the process described above, is shrunk radially by inserting a small diameter mandrel into the dilated tube and heating the tube at a predetermined temperature. The present inventors have found that by heating the dilated ePTFE tube over a small mandrel causes the dilated ePTFE tube to shrink radially around the mandrel thereby producing a tube which is homogeneous and has an inner diameter determined by the diameter of the mandrel. The only limitation on this process is that the mandrel cannot have a smaller diameter than the inner diameter of the initial ePTFE (i.e., the tube made by extrusion). Importantly, the tube contracted in this manner can be readily expandable by applying radial forces to it. In fact the tube can be expanded radially up to its original dilated size without causing it to lose strength or split. In other words, the plastic deformation limit of this tube is essentially the diameter of the dilated tube. The tube produced by this process is called herein a conformable ePTFE tube to differentiate it from other ePTFE tubes suggested by the prior art.

A further advantage of a conformable ePTFE tube is that its different longitudinal sections can be radially expanded independently of each other. For example, the ends of a tube can be expanded first, followed by the middle section extending between the ends. Moreover, these different sections need not be expanded to the same diameter.

An intraluminal device produced in accordance with this invention comprises a conformable ePTFE tube which is preferably supported by a self-expandable stent. In this manner, the intraluminal device or stent-graft itself is self-expandable after being deployed and thus will recover to its expanded diameter if it experiences any outside compressive forces.

The term 'self-expanding stents' refers to stents which, when released, increase in diameter automatically without the need for an external expansion means, such as a balloon or other similar means. Devices of this type include stents of braided wire, such as those taught by Wallsten U.S. Pat. No. 4,655,771, and stents of formed wire, such as those taught by Gianturco, U.S. Pat. No. 4,580,568. These stents expand to a large diameter after being released from a constraining force which restricts them to a smaller diameter. Self-expanding stents may be formed from nitinol wire as taught by PCT US 92/03481. These stents expand in diameter when exposed to a slight increase in temperature. The self-expanding stents employed in this invention are selected such that the radial force created when these stents are in their compressed state and inserted into a conformable ePTFE tube is less than the force needed to radially expand the conformable ePTFE tubes. The stents are further selected such that their maximum intended deployment diameter is less than their relaxed diameter, so that when deployed as intended (i.e. attached to a graft), they provide radial tension to the graft. In this manner, once the stents are affixed to a conformable ePTFE (as described more fully below), the tube is biased toward a cylindrical shape by the stent both before and after expansion.

The conformable ePTFE tubes and self-expanding stents may be adjoined when both devices are in their compressed state. Alternatively, a dilated PTFE tube and self-expanding stents may be adjoined first and then the ePTFE tube and the stents are contracted to a compressed size together. In either case, the production of said intraluminal devices is complete when the device is in its compressed state.

The conformable ePTFE tubes may be affixed to either the exterior surface or the luminal surface of the self-expanding stent. Alternatively, a first conformable ePTFE tube may be affixed to the exterior of the self-expanding stent and a second conformable ePTFE tube may be affixed to the luimnal position of the self-expanding stent. The first and second conformable ePTFE tubes may be affixed to each other in the spaces between or within the stents.

The conformable ePTFE tubes may also be affixed to the self-expanding stent with an adhesive. The adhesive may be a thermoplastic fluoropolymer adhesive such as fluorinated ethylene propylene (hereinafter FEP), perfluoroalkoxy (hereinafter PFA), polypropylene, or other similar material. The first and second PTFE tubes may then be affixed to each other by heating them above the crystalline melting point of the PTFE tubes adequately to cause the two coverings to thermally adhere, or alternatively they may be affixed by an adhesive such as FEP.

The stents may yet also be constrained between two tubes but be permanently affixed to neither. The two tubes are adhered to each other on their ends and in the spaces between and within the stents by thermal adhesion or fluoropolymer adhesive as described above.

The luminal device thus formed may be delivered percutaneously, typically through the vasculature, in its compressed state. Once reaching the intended delivery site, the tube (or tubes) and stents are radially and irreversibly expanded by a balloon or other means. In so doing, the self-expanding stents expand toward their relaxed diameter. However, as the stents do not reach their relaxed diameter, they remain in radial tension, biasing the tube against the vessel wall.

BRIEF DESCRIPTION OF THE DRAWINGS

FIG. 1 shows a flow chart for making a conformable ePTFE tube in accordance with this invention;

DESCRIPTION OF TILE PREFERRED EMBODIMENTS

Figure 2:
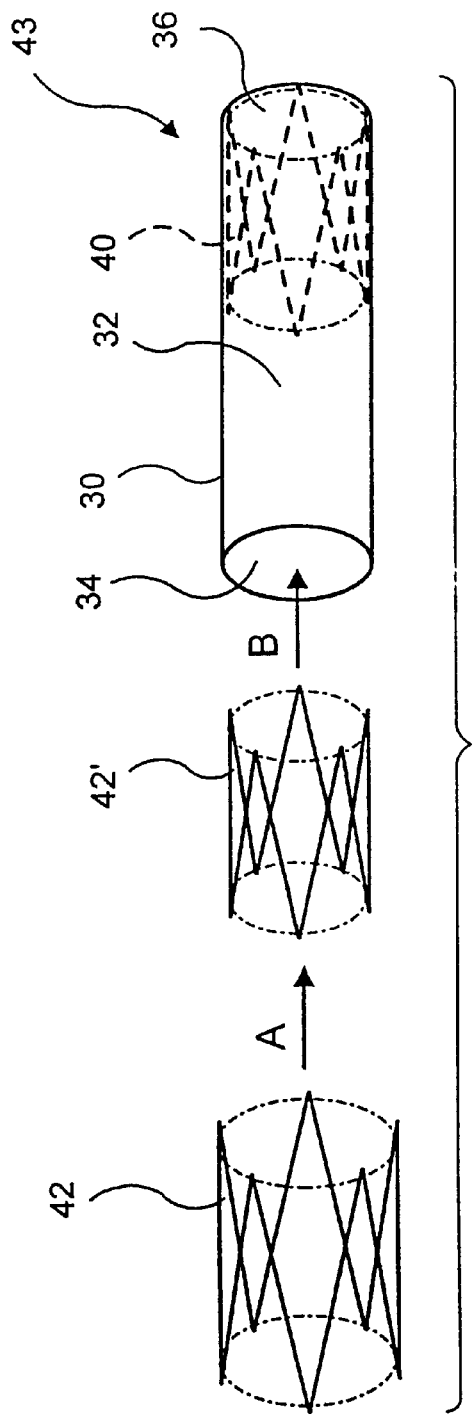
FIG. 2 shows an isometric view of a stent being radially contracted and inserted into the tube produced by the method of FIG. 1.

In accordance with this invention, an intraluminal device comprising a conformable ePTFE tube is made in three stages illustrated in FIG. 1. The first stage consists of making an initial ePTFE tube. This stage is well known in the prior art and is performed as follows:

a. A PTFE resin is compounded with a lubricant (preferably a petroleum distillate, such as naphtha);

b. The compound is compacted under pressure;

c. The compacted mass is extruded into a tube using a standard ram extrusion process to its predetermined diameter;

d. The tube is dried to remove the lubricant;

e. The dried tube is stretched longitudinally by up to 1000%;

f. The longitudinally stretched tube is sintered or cured at high temperature while its ends are fixed to insure that the tube does not shrink to its original length.

This stage is represented in FIG. 1 as step 10. As explained previously, because of various limitations associated with the extrusion process (including, for example the maximum extrusion force that can be generated by existing ram extruders) the resultant initial ePTFE tube has a relatively small diameter DI, of about 5–8 mm or a relatively thick wall (greater than 0.010 inches). Moreover, this tube cannot be readily expanded or dilated because it has a tendency to lose strength or split longitudinally when subjected to radial forces.

The next stage of the process is to dilate the initial ePTFE tube to a predetermined maximum diameter DM. This process of dilation involves progressively expanding the tube radially by a small, incremental amount at about 50° C. using a mandrel (step 12). After each incremental dilation, the tube is then calendered on a flat surface (step 14). If the tube has not reached a desired diameter, i.e., DM, as determined in step 16 then in step 18, it is removed from the mandrel and inserted over a next mandrel having an incrementally larger diameter. The steps 12–18 are repeated several times until a tube of a desired diameter DM is reached.

The resulting tube ePTFE can be made to very precise dimensions and is dimensionally stable. Importantly, tubes of diameters of 25 mm or more can be made using this process. Details of the procedure described so far are found in co-pending application to Colone et al. identified above.

However, in the present invention, a third stage is implemented to contract or shrink the dilated tube radially as follows. First, the dilated tube is removed from the mandrel having the diameter DM and inserted over a much smaller mandrel having a predetermined diameter DF (step 20). This diameter DF should not be smaller than the diameter DI of the initial ePTFE tube, i.e., at the end of step 10 in FIG. 1. For example, if after extrusion the initial ePTFE tube has a diameter of 4 mm, the diameter DF should be at least 4 mm or more.

Next, the tube on this smaller mandrel is heated at about 200° C. It was found that during this heating operation, the tube contracts radially until it hugs the mandrel. Typically this heating step may take about one to five minutes. Following heating, the tube can be removed from the mandrel (step 24). Importantly, the inventors have found that the resulting conformable tube maintains its last nominal diameter DF. However, if a radial force is applied internally to the tube by a balloon or other means, the conformable tube can be expanded to any diameter up to the maximum diameter DM established in step 16 without any physical damage.

FIG. 2 shows how to make an intraluminal device from a conformable tube and stents. First, a conformable PTFE tube 30 is prepared in accordance with the process described. Tube 30 includes a cylindrical sidewall 32 and two open ends 34, 36. Once tube 30 is completed, one or more stents are affixed to the tube 30. For example, in FIG. 2 stents 40, 42 are provided. The process of inserting the stent 42 into tube 30 is illustrated, with stent 40 having been already inserted. Each of these stents is formed of a thin wire filament made for example of a nickel titanium alloy such as nitinol. When relaxed, i.e., when they are not radially compressed or otherwise restrained in any manner, the stents have a generally tubular shape with a diameter much larger than the diameter of the tube 30. For example, for an endovascular stent placement procedure, the stents 40, 42 may have a relaxed diameter of 28 mm while the tube 30 may have a diameter of about 3 mm. Therefore, before or while the stents are inserted they must be compressed radially inwardly so that they can fit into the tube 30. In FIG. 2, tube 42 is first shown in its uncompressed state 42'. It is then compressed radially inwardly until it has been reduced in diameter, and then finally pushed into the tube 30, as indicated by arrow B resulting in an intraluminal device.

In order to insure that the stents 40 and 42 do not separate from the tube 30, an adhesive may be applied between the stents and the tube. A suitable adhesive for this purpose may be FEP, PFA, polypropylene or other similar materials.

Figure 3:
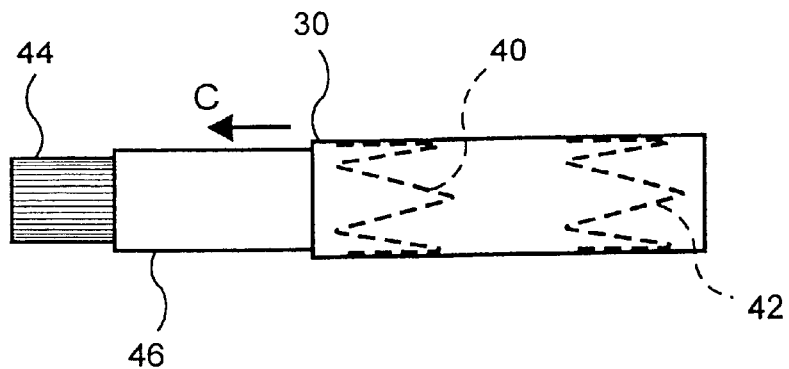
FIG. 3 shows an alternate embodiment of the invention wherein a contracted tube and two stents are positioned over a second contracted tube.
Figure 4:
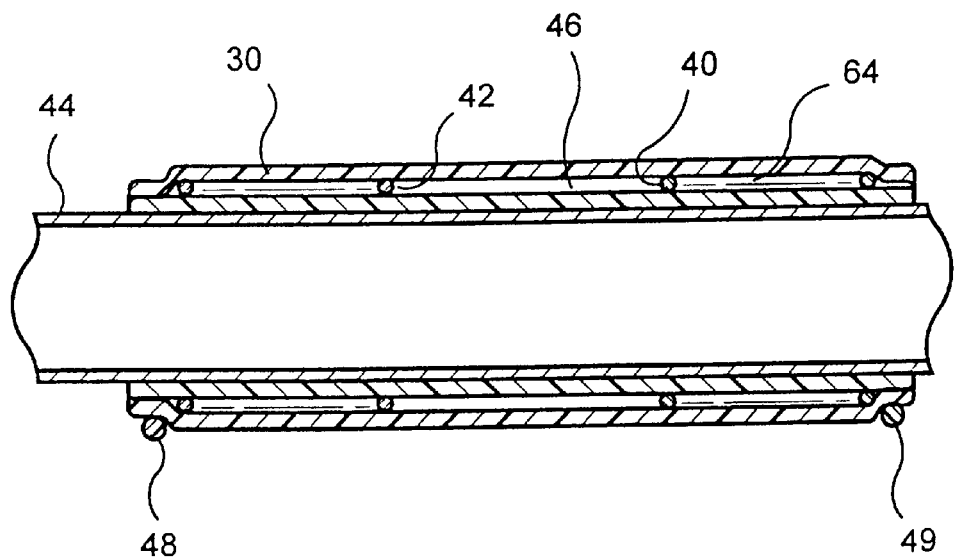
FIG. 4 shows an elevational sectional view of embodiment of FIG. 3.

Alternatively, the stents 40, 42 may be encapsulated between two tubes. For example, as shown in FIG. 3, a mandrel 44 may be provided with a tube 46 made in the same manner as tube 30 but having a slightly smaller outer diameter. Tube 30 with stents 40, 42 is then pulled telescopically over the tube 46 as indicated by arrow C until the tubes 30, 46 are co-extensive, as shown in FIG. 4.

Figure 5:
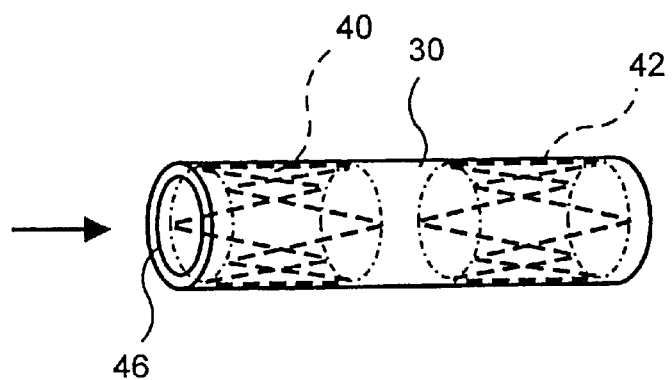
FIG. 5 shows an orthogonal view of the embodiment of FIGS. 3 and 4.

The two tubes 30 and 46 are then joined or bonded together. One method of bonding the two tubes 30, 46 is to apply a bonding or adhesive agent between these tubes, such as FEP or PFA. An alternative method is to sinter the two tubes together thereby allowing the walls of the tubes to adhere to each other. During sintering, in order to eliminate any potential creep, wires 48, 49 may be wound around the ends of the tubes prior to sintering. After the sintering is complete, the wires 48 and 49 can be removed. The resultant intraluminal device is shown in FIG. 5. Of course, the device of FIG. 5 may also be made by first positioning the stents 40, 42 over tube 46, pulling the tube 30 over the stents 40, 42 and tube 46 and then bonding the tubes 30, 46 together.

Figure 6:
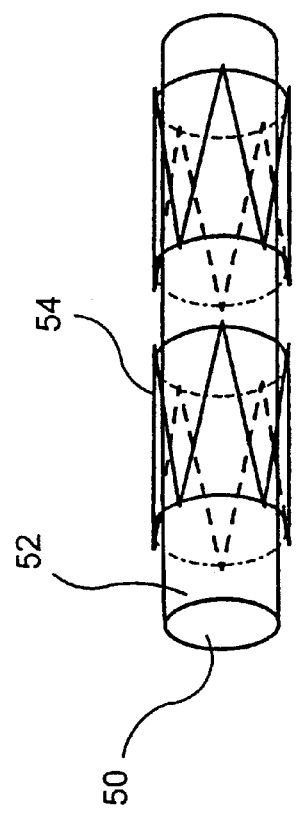
FIG. 6 shows another embodiment of the invention wherein a self-expandable stent is affixed externally to a conformable ePTFE tube.

In another alternate embodiment, shown in FIG. 6, a conformable ePTFE tube 50 is provided having an outer surface 52. In this embodiment one or more stents 54 are mounted on and secured to the outer surface 52. As in the embodiments of FIG. 2–5, the stent 54 has a relaxed configuration in which it has a diameter much larger than the diameter of the tube 50. The stent 54 can be installed by first positioning it over the tube 50, collapsing it radially inwardly until the stent 54 contacts the outer surface 52. The stent 54 can then be secured to the tube 50 by using an adhesive as described above.

Figure 7:
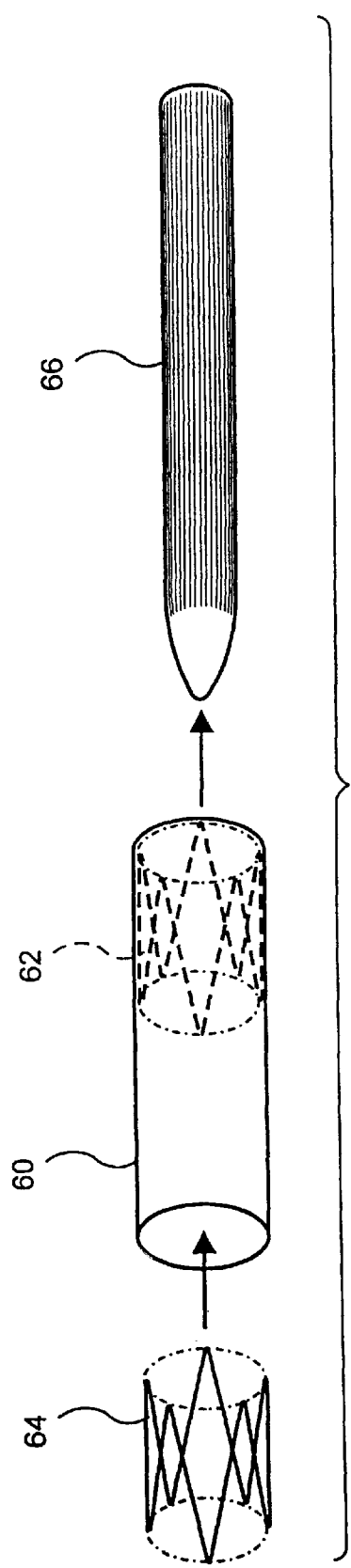
FIG. 7 shows an orthogonal view of a self-expandable stent affixed to a dilated tube, and the positioning of both over a small-diameter mandrel.

In yet another embodiment, referring to FIG. 7, an intraluminal device is produced as follows. First a dilated ePTFE tube 60 is provided by using steps 10–16 of the process of FIG. 1. Tube 60 may have a nominal diameter of about 25 mm. Next, two self-expanding stents 62 and 64 similar to stents 40, 42 are inserted into the tube 60. On the left side of FIG. 7, stent 62 has already been inserted into the tube 60. Preferably the stents 62, 64 have a slightly larger diameter then tube 60, of, for instance, 28 mm so that they apply a radial tensioning force on tube 60. Next, the tube 60 with stents 62, 64 is positioned on a small diameter mandrel 66. If the tube 60 was obtained from an initial ePTFE tube of 4 mm in steps 10–16 then mandrel 66 has a diameter of about 4–6 mm.

Figure 8:
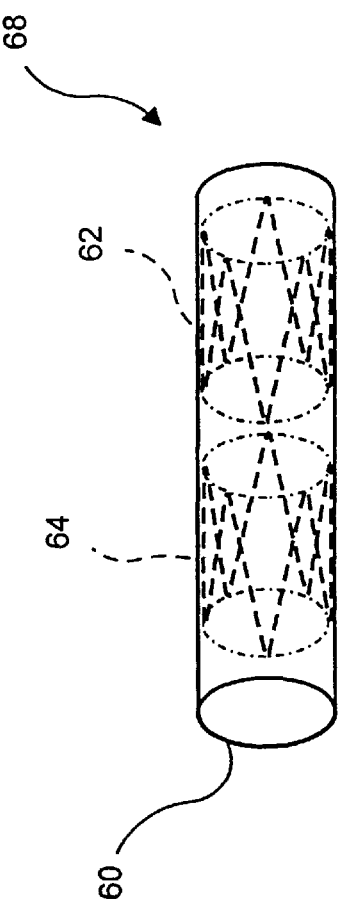
FIG. 8 shows an orthogonal view of a stent graft resulting from the operation of FIG. 7.

Next, the tube 60, the mandrel 66 and the stents 62 and 64 are placed into an oven heated to about 200° C. The mandrel 66 and the other components are kept in the oven until the tube 60 shrinks down to the size of mandrel 66. In this contracting process, as the mandrel shrinks, it automatically collapses the stents 62, 64 as well. When the contracting process is complete, the mandrel 66 is withdrawn leaving the intraluminal device 68, shown in FIG. 8. The device 68 in FIG. 8 is essentially identical in structure to the device 43 in FIG. 2, the only difference being the manner in which the two stent grafts are produced.

The intraluminal devices of FIGS. 5 and 6 may also be produced by assembling the ePTFE tube(s) and stent(s) together before the ePTFE tubes are contracted. In each of these embodiment suitable means, such as an adhesive, may have to be provided to insure that the stents and tubes do not disassociate during the contraction.

To summarize, an intraluminal device is formed in accordance with this invention by first producing a novel conformable ePTFE tube and then assembling this tube with one or more self-expandable stents in such a manner that the composite graft has a smaller diameter than the relaxed diameter of the stents. The stents can be either inside the conformable ePTFE tube, outside the conformable EPTFE tube or can be disposed or captured between two conformable ePTFE tubes. Importantly, the conformable ePTFE tubes have a maximum dilation diameter to which it can be safely expanded, which maximum diameter is smaller than the relaxed diameter of the stents. The intraluminal device formed is packaged for storage and shipping.

The intraluminal device is used as follows. First, the device is delivered percutaneously to a body vessel that needs to be repaired, using a suitable catheter. Next, a standard balloon such as an embolectomy or angioplasty balloon is inserted into the device and the balloon is inflated slowly until the device has the same diameter as the vessel, at which point the balloon is deflated and removed. Other known mechanical means of expanding the device may be used as well.

The intraluminal device must be chosen so that the maximum dilation diameter of the tube is equal to, or larger than the vessel diameter. As the device is expanded radially by the balloon, the stents affixed to the tube are expanded as well. Since the stents are self expanding, they maintain their tubular shape and do not collapse after the balloon is deflated and removed. Moreover, since the diameter of the device is always smaller than the relaxed diameter of the stents, the stents are always radially tensioned, thereby biasing the conformable ePTFE tube radially outwardly. Of course, this radial force from the stents on the tube is much smaller than the force required to expand the tube further. Therefore the stents provide support for the tube and keep it open while the vessel resumes its normal function.

The actual process for expanding the device depends on its diameter and length. If the device is short, it may be expanded in a single operation. If it is a long device, then it can be expanded in three or more stages. During the first two stages, the ends of the device are expanded to engage the vessel and anchor the device to the vessel. Then the center portion of the device is expanded. This process is described in detail in commonly assigned co-pending application S.N. 08/885,626 filed Jun. 30, 1997 entitled MULTIPLE DIAMETER EXPANDABLE GRAFT FOR BLOOD VESSEL AND METHOD OF DEPLOYING THE SAME, now U.S. Pat. No. 6,098,630.

Obviously numerous modifications may be made to this invention without departing from its scope as defined in the appended claims.

While the invention has been illustrated and described in detail in the drawings and foregoing description, the same is to be considered as illustrative and not restrictive in character, it being understood that only the preferred embodiment has been shown and described, and that all changes and modifications that come within the spirit of the invention are desired to be protected.

We claim:

1. An intraluminal device for insertion into a patient's vessel, said device comprising:

a conformable ePTFE tube having a predetermined diameter and length and capable of being radially expanded up to a diameter of said vessel.

2. The device of claim 1 further comprising a self-expandable stent affixed to said conformable ePTFE tube.

3. The device of claim 2 wherein said self-expandable stent has relaxed diameter formed when said self-expandable stent is not associated with said tube, said relaxed diameter being larger than said predetermined diameter.

4. An intraluminal device for insertion into a patient's vessel and comprising:

a comfortable ePTFE tube adapted to be radially expandable when an expansion force is applied; and a compressed self-expandable stent affixed to said tube, said stent generating a radial force on said tube which is smaller than said expansion force.

5. The device of claim 4 wherein said stent is disposed inside said tube.

6. The device of claim 4 wherein said stent is disposed outside said tube.

7. An intraluminal device comprising:

an outer conformable ePTFE tube expandable in response to an expansion force;

inner conformable ePTFE tube, positioned concentrically within the outer tube;

a self-expanding stent confined between the inner and outer tubes wherein the inner and outer tubes are adhered to each other.

8. The device of claim 7 wherein said stent is compressed and the radial force of the compressed stent is below said expansion force.

9. A method of producing an intraluminal device comprising:

providing a conformable ePTFE tube capable of being expanded to a predetermined diameter without exceeding its plastic deformation limit;

providing a self-expanding stent; and affixing said stent to said tube;

wherein the radial force required to expand said tube is greater than the radial force of the compressed stent member.

10. The method of claim 9 wherein said conformable ePTFE tube is formed by providing a dilated ePTFE tube and compressing said tube to a small diameter.

11. The method of claim 10 wherein said dilated ePTFE tube has a dilated diameter and where said predetermined diameter corresponds to said dilated diameter.

12. The method of claim 11 wherein said stent has a relaxed diameter defined when said stent is not compressed, said relaxed diameter being larger than said predetermined diameter, whereby after said radial expansion, said tube is biased into a cylindrical shape by said stent.

13. The method of claim 10 wherein said stent is affixed to said tube after the contraction of said tube.

14. The method of claim 9 wherein said stent is affixed after inserting said stent into said tube.

15. The method of claim 9 wherein said stent is affixed to an outer surface of said tube.

16. The method of claim 9 wherein said stent is adhesively affixed to said tube.

17. A method of producing an intraluminal device comprising:

providing an outer conformable ePTFE tube;

positioning at least one, self-expanding stent within said outer tube; providing an inner radially conformable ePTFE tube; positioning said inner tube concentrically inside said outer tube and said compressed stent; and adhering said inner and outer tubes to each other.

18. The method of claim 17 wherein said steps of providing said conformable ePTFE tubes includes providing corresponding dilated ePTFE tubes and contracting said dilated tubes to form said conformable ePTFE tubes.

19. The method of claim 18 wherein said stent is inserted into said outer tube after said outer tube is contracted.

20. The method of claim 18 wherein said stent is inserted into said outer tube before said outer tube is contracted.

21. The method of claim 17 wherein said step of adhering includes heating said tubes.

22. The method of claim 17 wherein said step of adhering includes providing an adhesive.

23. A method of producing a conformable ePTFE tube adapted for use as an intraluminal device by inserting said tube into a patient's vessel and expanding said conformable ePTFE tube radially to conform to a diameter of said vessel, said method comprising the steps of:

providing an initial ePTFE tube of a first diameter;

dilating said initial tube radially to form a dilated tube having a second diameter; and contracting said dilated tube to form said conformable tube having a third diameter, said conformable tube being radially expandable up to said second diameter without exceeding the plastic expansion limit of said final tube.

24. The method of claim 23 wherein said initial tube is formed by:

extruding ePTFE material into an extruded tube; and stretching said extruded tube longitudinally.

25. The method of claim 23 wherein said dilated tube is produced by expanding said initial tube incrementally, and calendering said tube between each expansion until said second diameter is reached.

26. The method of claim 23 wherein said dilated tube is contracted by inserting a mandrel into said dilated tube and sintering said dilated tube at a predetermined temperature.

27. The method of claim 26 wherein said mandrel has a mandrel diameter equal to said third diameter.

28. The method of claim 23 wherein said first diameter is in the range 1–10 mm, said second diameter is in the range of 4–30 mm and said third diameter is larger than 4 mm.

* * * * *